US007785354B2

(12) United States Patent
Biedermann et al.

(10) Patent No.: US 7,785,354 B2
(45) Date of Patent: Aug. 31, 2010

(54) BONE SCREW

(75) Inventors: Lutz Biedermann, VS-Villingen (DE); Jürgen Harms, Karlsruhe (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 806 days.

(21) Appl. No.: 11/291,920

(22) Filed: Dec. 2, 2005

(65) Prior Publication Data
US 2006/0084995 A1 Apr. 20, 2006

Related U.S. Application Data

(60) Division of application No. 10/763,431, filed on Jan. 22, 2004, which is a continuation of application No. 10/037,698, filed on Nov. 9, 2001, now Pat. No. 6,736,820.

(30) Foreign Application Priority Data

Nov. 10, 2000 (DE) ................. 100 55 888
Dec. 27, 2000 (DE) ................. 100 65 397

(51) Int. Cl.
*A61F 2/30* (2006.01)
(52) U.S. Cl. .............. 606/279; 606/266; 606/278
(58) Field of Classification Search .......... 606/61, 606/60, 69, 70, 71, 72, 73, 78, 266, 269, 606/264, 254, 278, 279, 246, 256, 301, 86 A
See application file for complete search history.

(56) References Cited

U.S. PATENT DOCUMENTS

| 4,484,570 A | 11/1984 | Sutter |
| 4,805,602 A | 2/1989 | Puno |
| 4,946,458 A | 8/1990 | Harms |
| 5,057,111 A | 10/1991 | Park |
| 5,084,048 A | 1/1992 | Jacob |
| 5,129,388 A | 7/1992 | Vignaud |
| 5,133,717 A * | 7/1992 | Chopin ................ 606/61 |
| 5,176,678 A | 1/1993 | Tsou |
| 5,190,543 A | 3/1993 | Schlapfer |
| 5,207,678 A | 5/1993 | Harms |
| 5,217,497 A | 6/1993 | Mehdian |
| 5,246,442 A | 9/1993 | Ashman |
| 5,253,406 A | 10/1993 | Shere |
| 5,344,422 A | 9/1994 | Frigg |
| 5,360,431 A | 11/1994 | Puno |

(Continued)

FOREIGN PATENT DOCUMENTS

CA    2216955    2/2004

(Continued)

OTHER PUBLICATIONS

Carbone's Response to European Office Action of Dec. 20, 2005, directed to EP Application No. 02 292 236.3; 8 pages.

(Continued)

*Primary Examiner*—Pedro Philogene
(74) *Attorney, Agent, or Firm*—Morrison & Foerster LLP

(57) ABSTRACT

A bone screw having a screw member possessing a threaded section and a head and a receiving part at the head end for receiving a rod to be connected to the bone screw is provided. The receiving part has on open first bore and a substantially U-shaped cross-section having two free legs provided with a thread. Furthermore, the receiving part has a second bore on the end opposite to the first bore whose diameter is greater than that of the threaded section and smaller than that of the head. On the bottom of the first bore a seat for the head is provided. In order that the screw member can be pivoted to at least one side by an enlarged angle, the edge bounding the free end of the second bore viewed relative to the axis of the first bore is of asymmetric construction.

24 Claims, 1 Drawing Sheet

U.S. PATENT DOCUMENTS

| | | | |
|---|---|---|---|
| 5,403,314 A | | 4/1995 | Currier |
| 5,439,381 A | | 8/1995 | Cohen |
| 5,443,467 A | | 8/1995 | Biedermann |
| 5,466,237 A | | 11/1995 | Byrd, III |
| 5,474,551 A | * | 12/1995 | Finn et al. ............... 606/61 |
| 5,474,555 A | | 12/1995 | Puno |
| 5,476,464 A | | 12/1995 | Metz-Stavenhagen |
| 5,486,176 A | | 1/1996 | Hildebrand et al. |
| 5,496,321 A | | 3/1996 | Puno |
| 5,531,746 A | | 7/1996 | Errico |
| 5,549,608 A | | 8/1996 | Errico |
| 5,554,157 A | | 9/1996 | Errico |
| 5,584,831 A | | 12/1996 | McKay |
| 5,586,984 A | | 12/1996 | Errico |
| 5,591,166 A | | 1/1997 | Bernhardt |
| 5,609,593 A | | 3/1997 | Errico |
| 5,647,873 A | | 7/1997 | Errico |
| 5,669,911 A | | 9/1997 | Errico |
| 5,672,176 A | | 9/1997 | Biedermann |
| 5,690,630 A | | 11/1997 | Errico |
| 5,725,527 A | | 3/1998 | Biedermann |
| 5,725,528 A | | 3/1998 | Errico |
| 5,728,098 A | * | 3/1998 | Sherman et al. ............. 606/269 |
| 5,733,285 A | | 3/1998 | Errico |
| 5,733,286 A | | 3/1998 | Errico |
| 5,735,850 A | | 4/1998 | Baumgartner |
| 5,735,852 A | | 4/1998 | Amrein |
| 5,752,957 A | | 5/1998 | Ralph |
| 5,797,911 A | | 8/1998 | Sherman |
| 5,810,818 A | | 9/1998 | Errico |
| 5,873,878 A | | 2/1999 | Harms |
| 5,879,350 A | | 3/1999 | Sherman |
| 5,882,350 A | | 3/1999 | Ralph |
| 5,885,286 A | | 3/1999 | Sherman |
| 5,891,145 A | | 4/1999 | Morrison |
| 5,946,988 A | | 9/1999 | Metz-Stavenhagen |
| 5,951,533 A | | 9/1999 | Freeman |
| 5,954,725 A | | 9/1999 | Sherman |
| 5,989,254 A | | 11/1999 | Katz |
| 5,997,539 A | | 12/1999 | Errico |
| 6,030,389 A | | 2/2000 | Wagner |
| 6,053,917 A | | 4/2000 | Sherman |
| 6,063,089 A | | 5/2000 | Errico et al. |
| 6,063,090 A | | 5/2000 | Schläpfer |
| 6,074,391 A | | 6/2000 | Metz-Stavenhagen |
| 6,077,262 A | | 6/2000 | Schläpfer |
| 6,090,110 A | | 7/2000 | Metz-Stavenhagen |
| 6,090,111 A | | 7/2000 | Nichols |
| 6,113,601 A | | 9/2000 | Tatar |
| 6,139,550 A | | 10/2000 | Michelson |
| 6,280,442 B1 | | 8/2001 | Barker |
| 6,299,614 B1 | * | 10/2001 | Kretschmer et al. ......... 606/264 |
| 6,325,802 B1 | | 12/2001 | Frigg |
| 6,443,953 B1 | | 9/2002 | Perra |
| 6,471,705 B1 | | 10/2002 | Biedermann |
| 6,485,491 B1 | | 11/2002 | Farris |
| 6,520,963 B1 | | 2/2003 | McKinley |
| 6,554,834 B1 | | 4/2003 | Crozet |
| 6,736,820 B2 | | 5/2004 | Biedermann et al. |
| 6,755,830 B2 | | 6/2004 | Minfelde et al. |
| 6,974,460 B2 | * | 12/2005 | Carbone et al. ............. 606/61 |
| 2001/0034522 A1 | | 10/2001 | Frigg |
| 2002/0091386 A1 | | 7/2002 | Martin |
| 2002/0183748 A1 | | 12/2002 | Martin |
| 2003/0045879 A1 | | 3/2003 | Minfelde et al. |
| 2003/0055426 A1 | | 3/2003 | Carbone |
| 2004/0243126 A1 | | 12/2004 | Carbone |
| 2005/0080420 A1 | | 4/2005 | Farris |
| 2005/0283157 A1 | | 12/2005 | Coates et al. |
| 2008/0132953 A1 | | 6/2008 | Carbone et al. |

FOREIGN PATENT DOCUMENTS

| | | | |
|---|---|---|---|
| DE | 19542116 A1 | 5/1997 | |
| EP | 0582857 | 2/1994 | |
| EP | 0885598 A2 | 12/1996 | |
| EP | 1023873 A2 | 8/2000 | |
| EP | 1090595 A2 | 9/2000 | |
| EP | 1273270 * | 1/2003 | .............. 606/61 |
| EP | 1273270 A1 | 1/2003 | |
| FR | 2802796 | 6/2001 | |
| JP | 6-142115 A | 5/1994 | |
| JP | 8-511189 | 11/1996 | |
| WO | WO-88/03781 | 6/1988 | |
| WO | WO-95/25474 | 9/1995 | |
| WO | WO-98/34554 | 8/1998 | |
| WO | WO-99/65415 | 6/1999 | |
| WO | WO-01/6940 A1 | 7/2000 | |
| WO | WO-01/58370 A1 | 1/2001 | |
| WO | WO-01/47425 | 7/2001 | |
| ZA | 98/3429 | 11/1998 | |

OTHER PUBLICATIONS

Carbone's Response to European Office Action of Apr. 26, 2005, directed to EP Application No. 02 292 236.3; 9 pages.

European Office Action dated Dec. 20, 2005, directed to EP Application No. 02 292 236.3; 3 pages.

Office Action dated Apr. 8, 2004, from the European Patent Office in Carbone's counterpart application.

Office Action mailed Jul. 1, 2004, issued in Carbone's U.S. Appl. No. 10/091,068.

Amendment filed on Aug. 11, 2004, in Carbone's U.S. Appl. No. 10/091,068.

European Office Action mailed on Apr. 26, 2005 relating to European Application No. 02 292 236.3 - 1265.

Japanese Notice of Grounds of Rejection mailed on Apr. 8, 2008, directed to JP Application No. 2001/343431.

Expert Report of Dr. Bret Ferree in *Stryker Spine* v. *Biedermann Motech et al.*, Civil Action No. 1:08-cv-1827-CKK, D.D.C., Apr. 2, 2009.

Deposition of Dr. Bret Ferree in *Stryker Spine* v. *Biedermann Motech et al.*, Civil Action No. 1:08-cv-1827-CKK, D.D.C., Apr. 30, 2009.

Biedermann et al., U.S. Office Action, mailed Oct. 16, 2007, directed to U.S. Appl. No. 11/319,427; 17 pages.

Biedermann et al. U.S. Office Action, mailed Jun. 3, 2008, directed to U.S. Appl. No. 11/319,427; 6 pages.

Biedermann et al., U.S. Office Action, mailed Dec. 11, 2008, directed to U.S. Appl. No. 11/319,427; 9 pages.

Biedermann et al.U.S. Office Action, mailed May 28, 2009, directed to U.S. Appl. No. 11/319,427:8 pages.

Biedermann et al., U.S. Office Action, mailed Oct. 11, 2006, directed to U.S. Appl. No. 10/763,431; 19 pages.

Motion of Plaintiff Stryker Spine for Summary Judgment Regarding Defendant's Failure to Comply with 35 U.S.C. § 112, filed on May 29, 2009; Civil Action No. 08-1827-CKK, 54 pages.

Motion of Plaintiff Stryker Spine for Summary Judgment Regarding Unpatentability of Defendants' Claims Under 35 U.S.C. §§ 102 and 103, filed on May 29, 2009; Civil Action No. 08-1827-CKK, 43 pages.

Defendant's Motion for Summary Judgment as to Each of Stryker Spine's Claims and Demands for Relief, filed on May 29, 2009; Case No. 1:08-cv-1827-CKK, 87 pages.

Defendant's Reply in Support of Their Motion for Summary Judgment as to Each of Stryker Spine's Claims and Demands for Relief, filed on Jul. 6, 2009; Case No. 1:08-cv-1827-CKK, 58 pages.

Reply of Plaintiff Stryker Spine in Further Support of Its Contingent Motion for Summary Judgment Regarding Defendant's Failure to Comply with 35 US.C. § 112, filed on Jul. 6, 2009; Case No. 1:08-cv-1827-CKK, 16 pages.

Reply of Plaintiff Stryker Spine in Further Support of Its Motion for Summary Judgment Regarding the PTO's Erroneous Refusal to Redefine the Interference "Count," filed on Jul. 6, 2009; Case No. 1:08-cv-1827-CKK, 30 pages.

Reply of Plaintiff Stryker Spine in Further Support of Its Contingent Motion for Summary Judgment or, in the Alternative, for Remand Regarding Unpatentability of Defendant's Claims Under 35 U.S.C. §§ 102 and 103, filed on Jul. 6, 2009; Civil Action No. 08-1827-CKK, 20 pages.

Letter from R. Wepner to B. Bretschneider and L. Dauchot dated Nov. 2, 2009, Regarding Civil Action No. 08-1827-CKK, D.D.C. 6 pages.

* cited by examiner

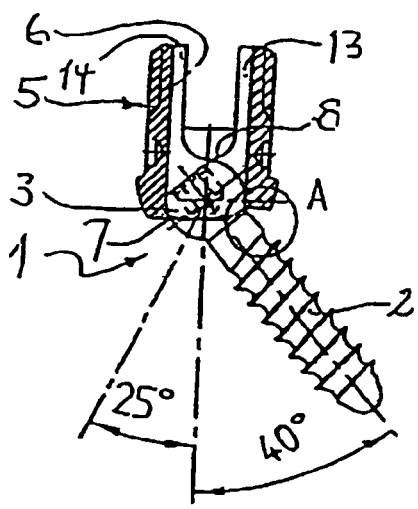
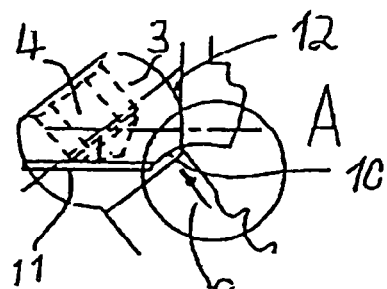
Fig. 1
Fig. 2
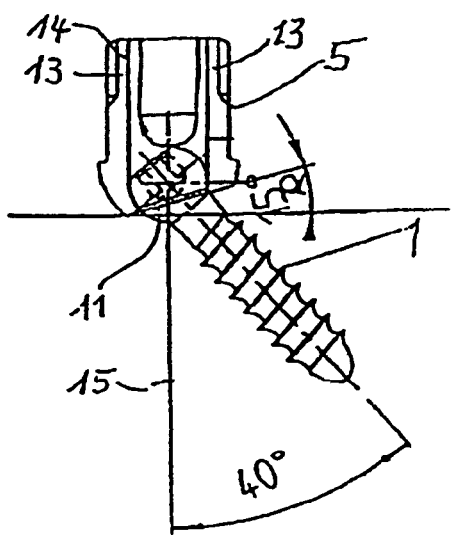
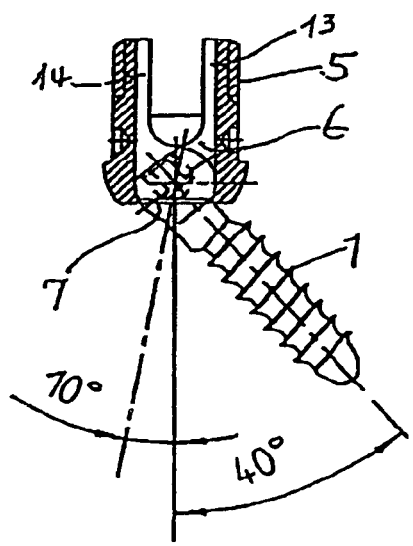
Fig. 3
Fig. 4

BONE SCREW

REFERENCE TO RELATED APPLICATIONS

This application is a division of Ser. No. 10/763,431, filed Jan. 22, 2004, which is a continuation of Ser. No. 10/037,698, filed Nov. 9, 2001, now U.S. Pat. No. 6,736,820, the disclosure of which is incorporated herein by reference.

FIELD AND BACKGROUND OF THE INVENTION

The invention relates to a bone screw having a threaded section and a head and a receiving part at the head end for receiving a rod to be connected to the bone screw, the receiving part possessing an open first bore and a substantially U-shaped cross-section having two free legs provided with a thread and a second bOre at the end opposite to the first bore, whose diameter is greater than that of the threaded section and smaller than that of the head and which forms the seat for the head, and a nut or screw working together with the thread.

Such a bone screw is disclosed, for example, in U.S. Pat. No. 5,672,176. In the known bone screw the head is of spherical segment-shaped construction. The bottom of the first bore adjacent to the second bore is likewise of spherical segment-shaped construction so that the spherical head lies on this spherical section. The plane going through the bounding edge is oriented at right angles to the axis of the first bore and the mid-point of the second bore coincides with the axis of the first bore. By this means it is achieved that the threaded section possessing the head is pivotable in a predetermined angle of generally up to 25° about the axis of the first bore so that even after screwing the threaded section into a vertebral segment orientation of the receiving part receiving a rod is possible. At the same time, the size of the pivot angle is limited to the extent that the second bore as a function of the diameter of the head must not exceed d certain size so that the head still has an adequate hold in the receiving part.

The use of such bone screws is something of a problem in the region of cervical vertebrae. In this case, due to the small dimensions of the cervical vertebrae, it is necessary that the screws must always be pivoted to one side and upwards, a greater degree of pivoting being necessary than is the case in the larger thoracic vertebrae and lumbar vertebrae.

SUMMARY OF THE INVENTION

The aim of the invention is to provide a bone screw which permits a larger pivot angle. This task is solved by a bone screw having a screw member that possess a threaded section, a head and a receiving part at the head end for receiving a rod to be connected to the bone screw. The receiving part has an open first bore and a substantially U-shaped cross-section having two free legs provided with threads, a second bore at the end opposite the first bore having a diameter greater than the diameter of the threaded section and smaller than the diameter of the head, and a seat for the head and a nut or screw acting together with the thread. When viewed relative to the axis of the first bore, the edge bounding the free end of the second bore is asymmetrical.

Refinements of the invention are identified in the more detailed embodiments described below.

BRIEF DESCRIPTION OF THE DRAWINGS

Further features and practical advantages of the invention emerge from the description of exemplified embodiments with reference to the figures.

FIG. 1 depicts a side elevation of a first embodiment of the invention, partly in sectional representation.

FIG. 2 shows an enlarged detail of FIG. 1.

FIG. 3 depicts a side elevation, partly in sectional representation, of a second embodiment of the invention.

FIG. 4 depicts a corresponding representation of a further embodiment of the invention.

DETAILED DESCRIPTION OF THE INVENTION

The bone screw includes a screw member proper 1 having a threaded section 2 and a head 3. The head is formed in the shape of a segment of a sphere in the region adjoining the threaded section. Coaxial with the thread axis and on the end opposite to the threaded section 2 the head possesses a recess 4 for engagement with a socket screw key.

The bone screw further comprises a cylindrically constructed receiving part 5. At one end this has a first bore 6 of axially symmetrical construction. On the opposite end a second bore 7 is provided whose diameter is greater than that of the threaded section 2 and smaller than that of the head 3. On the end opposite to the second bore the first bore is open and its diameter is of such a size that that the screw member 1 can be guided through the open end by its threaded section 2 going through this bore and by the head going as far as the bottom of the first bore. The bottom of the first bore is constructed as a spherically shaped region towards the open end, the radius being substantially equal to the radius of the spherical segment-shaped section of the head 3. Furthermore, the receiving part 5 has a U-shaped recess 8 arranged symmetrically relative to the center of the part whose bottom is directed towards the second bore 7 and whose two side legs 13, 14 extend to the open end directed towards the first bore 6. At the free end of the legs 13, 14 a thread for engagement with a screw member constructed as a nut or screw is provided. The nut or screw serves to fix a rod to be inserted into the U-shaped recess 8, it being possible for the nut or screw to act on the rod directly or via a pressure member.

In the embodiment shown in FIGS. 1 and 2, in the direction of the arrow 9, whose direction lies in a plane going through the axis of symmetry of the first bore and which is inclined to the axis of symmetry by a predetermined angle, a circular countersink 10 is made in the edge between the opening plane 11 of the second bore and the edge 12—of the first bore.

In this manner, as can be seen in the figures, it is achieved that the angle between the axis of the screw member 1 and the axis of symmetry of the first bore is substantially enlarged by comparison with the angle otherwise attainable. At the same time the seat of the screw member 1 in the receiving part is retained.

In the second embodiment shown in FIG. 3 the interior of the receiving part 5 is constructed as in the first embodiment. The opening plane 11, which bounds the second bore 7, in this embodiment is inclined at a predetermined angle α to the plane bounded by the second bore 7 so that the normal to this plane 11 and the axis of symmetry of the first bore 15 enclose the angle of inclination. In the case shown this angle α is 15° as an exemplified embodiment. In this version it is also achieved that the screw member 1 is pivotable in the direction shown by an angle to the axis of symmetry of the-first-bore which is substantially greater than the angle which is achievable in the usual mode of construction.

Both in the embodiment shown in FIG. 1 and the embodiment shown in FIG. 3 the countersink or chamfer is selected in such a way that in each case a small peripheral section still remains which still belongs to the spherical seat.

In a fourth embodiment which is not shown the mid-point of the second bore is constructed offset to the side to a small extent, for example by 0.5 mm, relative to the axis of symmetry of the first bore. This lateral offsetting in turn produces the result that the head is held in the mounting formed by the spherically constructed bottom but a greater pivot width is achieved in a side direction.

In the exemplified embodiments described above four different approaches to a solution are presented. It is also possible to combine the individual approaches with one another; that is, for example, to combine the solution according to the first and second exemplified embodiments or one of the two with the third and/or fourth exemplified embodiment, or even all four exemplified embodiments in order to achieve, in this way, a still greater possibility for pivoting in at least one direction.

In the exemplified embodiments described above the spherical bottom of the first bore 6 is constructed in each case as an integral component of the receiving part 5. In a modified embodiment, however, the spherical bottom can also be provided either in a mounting part introduced through the first bore 6 or in a mounting part introduced through the second bore 7. The invention is then used in a corresponding manner to the end that the receiving part together with the insert piece is regarded as one member and the measures described above are taken on this piece assembled in this way.

The members forming the bone screw are preferably made of titanium.

In the embodiment shown in FIG. 4 the edge bounding the free end of the second bore viewed relative to the axis of the first bore is of symmetrical construction. The asymmetry is achieved in that the screw 1 has a recess or countersink 16 on its neck engaging on the sphere or the spherical segment so that in the manner shown in FIG. 4 as in the exemplified embodiments previously described the enlarged pivot angle can be achieved.

What is claimed is:

1. A method of stabilizing bone comprising:
   providing a coupling element having first and second bore sections that are angled relative to one another, said coupling element having rod-receiving openings for receiving an elongated member;
   assembling said coupling element with an anchoring element;
   after the assembling step, securing said anchoring element in bone;
   moving said coupling element relative to said anchoring element to align said rod-receiving openings with said elongated member;
   securing said elongated member in said rod-receiving openings; and
   after the securing step, locking said coupling element from further movement relative to said anchoring element.

2. The method of claim 1, wherein said coupling element has a first bore extending through said first bore section and a second bore extending through said second bore section.

3. The method of claim 1, wherein said rod-receiving openings extend through said first bore section of said coupling element in a direction transverse to said first bore.

4. The method of claim 1, wherein said first and second bores intersect one another between said upper and lower ends of said coupling element.

5. The method of claim 1, wherein said elongated member is an orthopedic rod.

6. A method of stabilizing a spine, comprising:
   providing a coupling element having a first bore coaxial with a first longitudinal axis and extending through a first bore section of said coupling element and a second bore coaxial with a second longitudinal axis and extending through a second bore section of said coupling element, wherein said first and second longitudinal axes are transverse to one another;
   assembling said coupling element with an anchoring element; and
   after the assembling step, securing said anchoring element in bone.

7. The method of claim 6, wherein said coupling element has rod receiving openings for securing an orthopedic rod, the method further comprising:
   moving said coupling element relative to said anchoring element to align said rod-receiving openings with said orthopedic rod;
   securing said orthopedic rod in said rod-receiving openings; and
   after the securing step, locking said coupling element from further movement relative to said anchoring element.

8. The method as claimed in claim 6, wherein said coupling element has an upper end and a lower end, said first bore extending from said upper end toward said lower end and said second bore extending from said lower end toward said upper end.

9. The method as claimed in claim 8, wherein said first and second bores are in communication with one another between said upper and lower ends of said coupling element.

10. The method as claimed in claim 6, wherein said upper end of said coupling element defines a first plane and said lower end of said coupling element defines a second plane, and wherein said first and second planes intersect one another.

11. The method as claimed in claim 6, wherein said anchoring element is a separate member assembled with said coupling element so that said coupling element and said anchoring element are movable relative to one another.

12. The method as claimed in claim 6, wherein said anchoring element has a head having a substantially spherical underside, and wherein said coupling element has a seat at the lower end thereof 13. The method as claimed in claim 12, wherein said seat is shaped for facilitating pivotal movement of said coupling element and said anchoring element relative to one another.

14. The method as claimed in claim 13, wherein said seat has a substantially concave surface adapted to engage the spherical underside of said head.

15. A method of stabilizing a spine comprising:
   providing a coupling element having an uppermost end defining a first plane, a lowermost end defining a second plane, and at least one bore extending from said uppermost end toward said lowermost end, wherein said first and second planes intersect one another;
   assembling said coupling element with an anchoring element;
   after the assembling step, securing said anchoring element in bone.

16. The method as claimed in claim 15, wherein said coupling element has rod receiving openings for securing an orthopedic rod, the method further comprising:
   moving said coupling element relative to said anchoring element to align said rod receiving openings with said orthopedic rod;
   securing said orthopedic rod in said rod receiving openings; and
   after the securing step, locking said coupling element from further movement relative to said anchoring element.

17. The method as claimed in claim 15, wherein said at least one bore is adapted for receiving said anchoring element.

18. The method as claimed in claim 15, wherein said rod receiving openings are defined by substantially U-shaped opening surfaces.

19. A method of stabilizing a spine, comprising:
providing a coupling element having a first bore coaxial with a first longitudinal axis and a second bore coaxial with a second longitudinal axis, wherein said first and second longitudinal axes are transverse to one another and wherein said first and second bores are within an integral portion of said coupling element;
assembling said coupling element with an anchoring element having a head wherein a seat of said coupling element is adapted to contact an underside of said head, and wherein at least a portion of said anchoring element is capable of passing though both first and second bores; and
after the assembling step, securing said anchoring element in bone.

20. The method of claim 19, wherein said coupling element has rod receiving openings for securing an orthopedic rod, the method further comprising:
moving said coupling element relative to said anchoring element to align said rod-receiving openings with said orthopedic rod;
securing said orthopedic rod in said rod-receiving openings; and
after the securing step, locking said coupling element from further movement relative to said anchoring element.

21. The method as claimed in claim 19, wherein said coupling element has an upper end and a lower end, said first bore extending from said upper end toward said lower end and said second bore extending from said lower end toward said upper end.

22. The method as claimed in claim 19, wherein said upper end of said coupling element defines a first plane and said lower end of said coupling element defines a second plane, and wherein said first and second planes intersect one another.

23. The method as claimed in claim 19, wherein said anchoring element has a head having a substantially spherical underside, and wherein said seat of said coupling element is located at the lower end thereof.

24. The method as claimed in claim 23, wherein said seat is shaped for facilitating pivotal movement of said coupling element and said anchoring element relative to one another.

* * * * *